US006964852B2

(12) United States Patent
Jolivet et al.

(10) Patent No.: US 6,964,852 B2
(45) Date of Patent: Nov. 15, 2005

(54) ANTIGENIC STRUCTURAL PEPTIDE, ANTIGENIC AND IMMUNOGENIC COMPOUNDS, AND USES FOR DETECTING, PREVENTING AND TREATING AN HCV INFECTION

(75) Inventors: Michel Jolivet, Bron (FR); Francois Penin, Decines (FR); Pascal Dalbon, Lyons (FR); Laurent Ladaviere, Villeurbanne (FR); Xavier Lacoux, Lyons (FR)

(73) Assignee: Bio Merieux, Marcy (FR)

( * ) Notice: Subject to any disclaimer, the term of this patent is extended or adjusted under 35 U.S.C. 154(b) by 0 days.

(21) Appl. No.: 10/367,677

(22) Filed: Feb. 19, 2003

(65) Prior Publication Data

US 2003/0118604 A1 Jun. 26, 2003

Related U.S. Application Data

(60) Division of application No. 09/389,756, filed on Sep. 7, 1999, now Pat. No. 6,576,240, which is a continuation-in-part of application No. PCT/FR98/00442, filed on Mar. 5, 1998.

(30) Foreign Application Priority Data

Mar. 5, 1997 (FR) ............................. 97 02878

(51) Int. Cl.$^7$ ............................. G01N 33/53
(52) U.S. Cl. ................... 435/7.1; 435/5; 435/235.1; 424/189.1; 424/204.1; 424/228.1; 530/300; 530/403; 436/501
(58) Field of Search .................. 435/7.1, 5, 235.1; 424/189.1, 204.1, 228.1, 186.1, 93.2, 278.1; 530/300, 403, 350, 324, 826; 436/501

(56) References Cited

U.S. PATENT DOCUMENTS 6,235,284 B1   5/2001   Dalbon et al.

FOREIGN PATENT DOCUMENTS

| EP | 0 388 232 A1 | 9/1990 |
| EP | 0 569 309 A1 | 11/1993 |
| EP | 0 628 572 A2 | 12/1994 |

OTHER PUBLICATIONS

Abstract of JP 06 327 482 A, Nov. 29, 1994, Derwent Publications Ltd., London, GB, AN 95–047903.
Chemical Abstracts, vol. 119, No. 5, Aug. 2, 1993, Columbus, Ohio, US; Abstract No. 47025.
Ching, Wei–Mei et al., "Interaction of immune sera with synthetic peptides corresponding to the structural protein region of hepatitis C virus," *Proceedings of the National Academy of Sciences of USA*, vol. 89, pp. 3109–3194, Apr. 1992.
Cerino, Antonella et al., "A Human Monoclonal Antibody Specific for the N Terminus of the Hepatitis C Virus Nucleocapsid Protein," *Journal of Immunology*, vol. 151, No. 12, pp. 7005–7015, Dec. 15, 1993.
B. Hosein et al., "Improved serodiagnosis of hepatitis C virus infection with synthetic peptide antigen from capsid protein," *Proc. Natl. Acad. Sci. USA*, vol. 88, pp. 3647–3651 (1991).
L. Pauling et al., "The Structure of Proteins: Two Hydrogen–Bonded Helical Configurations of the Polypeptide Chain," *Proc. Natl. Acad. Sci. USA*, vol. 37, pp. 205–211 (1951).
P. Chou et al., "β–Turns in Proteins," *J. Mol. Biol.*, vol. 115, pp. 135–175 (1977).
J. Leszczynski et al., "Loops in Globular Proteins: A Novel Category of Secondary Structure," *Science*, vol. 234, pp. 849–855 (1986).
D. J. Lipman et al., "Rapid and Sensitive Protein Similarity Searches," *Science*, vol. 227, 1435–1441 (1985).
D. Marion et al., "Rapid Recording of 2D NMR Spectra without Phase Cycling. Application to the Study of Hydrogen Exchange in Proteins,"*J. Magn. Res.*, vol. 85, pp. 393–399 (1989).
C. Griesinger et al., "Clean TOCSY for H Spin System Identification in Macromolecules," *J. Am. Chem. Soc.*, vol. 110, pp. 7870–7873 (1988).
A. T. Brünger, "A System for X–ray Crystallography and NMR," *X–PLOR*, Yale University Press, New Haven (1992).

*Primary Examiner*—Laura Scheiner
(74) *Attorney, Agent, or Firm*—Oliff & Berridg, PLC

(57) ABSTRACT

The invention concerns a structural peptide, identified by antibodies directed against a polypeptide, comprising the 2–45 amino acid sequence of the N-terminal end of the Core or nucleocapsid (p21) protein of the hepatitis C virus (HCV), excluding any protein or peptide compound comprising or consisting of the N-terminal end. The invention is characterized in that it comprises a tertiary structure consisting of at least a first peptide fragment having a secondary structure in α helix, a second peptide fragment having secondary structure in α helix and a third peptide bond fragment linking the two α helices, these two α helices being substantially perpendicular to each other in space. This peptide can be used for detecting antibodies directed against the p21 protein of HCV, for detecting all of part of the RNA of HCV and for preparing a diagnostic, prophylactic or therapeutic composition for detecting, preventing or treating an HCV infection.

26 Claims, 7 Drawing Sheets

ANTIGENIC STRUCTURAL PEPTIDE, ANTIGENIC AND IMMUNOGENIC COMPOUNDS, AND USES FOR DETECTING, PREVENTING AND TREATING AN HCV INFECTION

This is a divisional application of U.S. application Ser. No. 09/389,756, filed Sep. 7, 1999 now U.S. Pat. No. 6,576,240, which is a Continuation-in-Part of International Application No. PCT/FR98/00442, filed Mar. 5, 1998. The entire disclosure of the prior applications is hereby incorporated by reference herein in its entirety.

The present invention relates to the characterization of an antigenic site belonging to an immunodominant multi-epitope region located in the N-terminal end of the Core or nucleocapsid protein (or p21 protein) of the hepatitis C virus (HCV), [B. Hosein et al., Proc. Natl. Acad. Sci. USA, 88, 3647–51 (1991)] as well as to the applications resulting therefrom, in particular in the diagnosis, treatment or prevention of an HCV infection.

In accordance with the document EP-A-0 569 309, in the name of the Applicant, a peptide is known which extends from the amino acid at position 2 to the amino acid at position 45 of the N-terminal end of the HCV nucleocapsid protein, and whose sequence is identified by SEQ ID NO: 1. This peptide determines an immunodominant region which is sufficient, on its own, for obtaining the same sensitivity and specificity, in terms of detection of antibodies directed against HCV, as with the nucleocapsid protein in its entirety.

Continuing its work on the peptide defined above, the Applicant has discovered that:

the region extending from amino acid 15 to amino acid 39 of the N-terminal end of the nucleocapsid protein defines the location of an immunodominant epitope, this immunodominant epitope is of conformational type, and corresponds to a three-dimensional unit of helix-loop or elbow-helix type, in which the two helices are arranged substantially perpendicularly to each other.

Thus, the invention relates to a structural peptide, recognized by the antibodies directed against a polypeptide comprising the sequence of amino acids 2–45 of the N-terminal end of the Core protein (p21) of the hepatitis C virus (HCV), which comprises, or consists of, a tertiary structure consisting of at least a first peptide fragment having a secondary structure in the form of an α helix, a second peptide fragment having a secondary structure in the form of an α helix and a third joining peptide fragment linking the two α helices, these two α helices being substantially perpendicular to each other in space. The angle formed by the two α helices is advantageously 90°±10°.

As used herein, the phrase "hepatitis C virus" includes all of the naturally occurring forms of hepatitis C virus.

The third joining peptide fragment is preferably chosen from loops and elbow-shaped secondary structures, in particular β elbows.

According to the present invention, are excluded from the preceding definition, and from the following definitions, all protein or peptide compounds comprising or consisting of the N-terminal end of the p21 protein, this end being considered as starting at the amino acids at position 1 or the amino acid at position 2. The excluded portion preferably includes at least the first 5 amino acids of the N-terminal end of the p21 protein (the first 4 amino acids of the N-terminal end of SEQ ID NO:1); more preferably at least the first 8 amino acids of the N-terminal end of the p21 protein (the first 7 amino acids of the N-terminal end of SEQ ID NO:1); even more preferably at least the first 11 amino acids of the N-terminal end of the p21 protein (the first 10 amino acids of SEQ ID NO:1); and most preferably the first 14 amino acids of the N-terminal end of the p21 protein (the first 13 amino acids of the N-terminal end of SEQ ID NO:1).

Advantageously, the peptide sequence of the peptide of the invention is chosen from any peptide sequence equivalent to SEQ ID NO: 2, such as SEQ ID NO: 3 to 10.

Preferably, the peptide contains fewer than 45 amino acids. More preferably, the peptide contains no more than 35 amino acids. Even more preferably the peptide contains no more than 30 amino acids. Most preferably, the peptide contains about 25 amino acids.

Advantageously, the peptide of the invention is different from the sequence SEQ ID NO: 11 (Gln Arg Lys Thr Lys Arg Asn Thr Asn Arg Arg Pro Gln Asp Val Lys Phe Pro Gly Gly Gly Gln Val Val Gly Gly Val Tyr Leu Leu Pro Arg).

Preferably, the peptide of the invention is different from fragment 4–39 of SEQ ID NO:1.

Before describing the present invention in greater detail and presenting the importance and the applications thereof, a definition of terms used in the description and the claims is given below.

Conformational epitope is understood to mean a protein region recognized by antibodies and determined in particular by amino acids which may be distant in the protein sequence but which, because of the folding of the polypeptide chain, become close to each other in space and may thus form a unit capable of being recognized by the antibody.

Peptide designates a stretch of amino acids which is obtained by chemical synthesis or by genetic recombination techniques. The peptides according to the invention may be obtained by conventional synthesis methods, for example with an automated peptide synthesizer, or by genetic engineering techniques comprising the insertion of a DNA sequence encoding said peptide into an expression vector such as a plasmid or a virus, and the transformation of eukaryotic or prokaryotic cells with this expression vector and culturing of these cells.

Peptide sequence equivalent to a reference peptide sequence (such as SEQ ID NO: 2 in the case of the present invention), said reference peptide sequence having a reference unit, is understood to mean an amino acid sequence modified by insertion and/or deletion and/or substitution and/or extension and/or shortening and/or chemical modification of one or more amino acids, as long as these modifications, on the one hand, substantially preserve, or even amplify, the antigenic properties of said reference peptide sequence and, on the other hand, essentially conserve the reference tertiary structure of said reference peptide sequence.

Thus, "equivalent sequence" is understood to mean in particular the sequences in which one or more amino acids are substituted by one or more other amino acids; the sequences in which one or more amino acids of the L series are replaced by one or more amino acids of the D series; the sequences into which there has been introduced a modification of the amino acid side chains, such as an acetylation of the amine functions, a carboxylation of the thiol functions, an esterification of the carboxyl functions, a substitution of an oxygen atom by a sulfur atom, and the like; a modification of the peptide bonds, such as carba, retro, inverse, retro-inverse, reduced and methyleneoxy bonds.

Peptide sequences equivalent to SEQ ID NO: 2 also comprise those of mimotope peptides which have a very different peptide sequence from SEQ ID NO: 2, while having the same antigenic properties and potentially the same tertiary structure as SEQ ID NO: 2.

Peptide sequences equivalent to SEQ ID NO: 2 also comprise those of mimotope peptides which have a peptide sequence little different from SEQ ID NO: 2, while having the same tertiary structure and the same antigenic properties as SEQ ID NO: 2. These mimotope peptides are described as an example by the peptide sequences SEQ ID NO: 3 to 10.

The secondary structure of a peptide fragment is defined as a three-dimensional structure essentially stabilized by hydrogen bonds involving the atoms which form the primary structure. Several types of secondary structures, and in particular the structure in the form of an α helix and the structure in the form of a β elbow, can be distinguished.

The α helix has been described by Pauling et al. [L. Pauling, Proc. Natl. Acad. Sci. USA, 37, 205–211 (1951)], and corresponds to a right-handed helix. The α helix is essentially stabilized by hydrogen bonds between the oxygen of the carbonyl group of the amino acid at position i and the hydrogen of the amide group of the amino acid at position i+4. These hydrogen bonds are almost parallel to the longitudinal axis of the helix, and the N, H and O involved in the hydrogen bond are practically colinear. The neighboring amino acid residues are 1.5 Å apart on the axis of the α helix, and a complete turn corresponds to 3.6 amino acid residues. The movement along the axis of the helix is therefore 5.4 Å per turn.

The parameters of the α-helix structure are the following:
Angles in degrees:

| | |
|---|---|
| $\phi$ | −57 |
| $\psi$ | −47 |
| $\omega$ | 180 |

Amino acids per turn 3.6,
Interresidue distance in Å ($C_{\alpha i}$–$C_{\alpha+1}$) 1.5

The β elbows are considered as a secondary structure of which at least 7 different types have been described-[P. Chou and G. D. Fasman, J. Mol. Biol., 115, 135–175 (1977)]. They allow the folding of the polypeptide chain and involve a minimum of 4 amino acids. They generally allow a change of direction between 2 secondary structures.

Finally, the loops, which are not generally considered as a secondary structure, correspond to a continuous segment of polypeptide chain most often describing the letter Ω in space, hence their name of omega loop [J. Leszczinski and J. Rose, Sciences, 234, 849–855 (1986)]. A loop is defined by its length and a short distance between its ends. The loops are stabilized and defined by interactions at the level of the side chains of their constituent residues.

To obtain a unit, or reference tertiary structure corresponding to the preceding definition according to the invention, it preferably comprises a primary structure equivalent to the amino acids extending from the amino acid at position 15 to the amino acid at position 39 of the N-terminal end of the nucleocapsid protein of the hepatitis C virus.

More advantageously, this primary structure comprises, or consists of, any peptide sequence equivalent to SEQ ID NO: 2. When the structural peptide has the primary structure identified by SEQ ID NO: 2, the first peptide fragment, having a secondary structure in the form of an α helix, consists of the sequence Thr Asn Arg Arg Pro Gln Asp Val Lys Phe (1 to 10), the second peptide fragment, having a secondary structure in the form of an α helix, consists of the sequence Gin Ile Val Gly Gly Val Tyr Leu Leu Pro Arg (15 to 25), and the third peptide fragment consists of the sequence Pro Gly Gly Gly (11 to 14).

The invention also relates to an antigenic compound, recognized by the antibodies directed against a polypeptide comprising, or consisting of, the sequence of amino acids 2–45 of the N-terminal end of the Core protein (p21) of the hepatitis C virus (HCV), as well as to an immunogenic compound capable of inducing the production of antibodies, said antigenic or immunogenic compound comprising a peptide of the invention, excluding any protein or peptide compound comprising or consisting of the N-terminal end of the p21 protein, this end being considered as starting at the amino acid at position 1 or the amino acid at position 2.

By way of examples, the peptide according to the invention may be conjugated, according to techniques well known to the person skilled in the art, with a carrier molecules such as, for example, a natural or recombinant protein, a synthetic polymer of amino acids or with aliphatic chains, a nucleic fragment or a tracer or marker molecule, such as, for example, an oligonucleotide, an enzyme, such as horseradish peroxidase, alkaline phosphatase or β-galactosidase or alternatively a radioelement. The peptide of the invention may be attached to any support.

The monoclonal or polyclonal antibodies capable of being obtained, for example, by immunization of an animal or immunization in vitro with the immunogenic compound defined above, under conventional physicochemical conditions, also constitute a subject of the present invention.

The subjects of the invention which are described above, namely antigenic or immunogenic compound and peptide are capable of being used for detecting and/or quantifying antibodies directed against the p21 of HCV, and the above-mentioned antibodies may be used for detecting and/or quantifying the antigens of HCV.

These subjects may, in addition, be applied to the preparation of a diagnostic, prophylactic or therapeutic composition intended for detecting, preventing or treating an infection with HCV.

Accordingly, the invention also relates to a pharmaceutical composition comprising a unit, a peptide, a compound, and/or antibodies defined above.

The invention relates, in addition, to:
 a method of detecting and/or quantifying, in a sample, either antibodies directed against the HCV nucleocapsid protein, or antigens of HCV, comprising the steps consisting in bringing said sample into contact with, either a peptide and/or a compound defined above, or antibodies of the invention, and in detecting the formation of an immune complex, either between said antibodies and said peptide or compound, or between said antigens and said antibodies of the invention;
 a method of detecting and/or quantifying, in a sample, all or part of the HCV RNA, comprising the steps consisting in bringing said sample into contact with a peptide, and/or a compound of the invention, and in detecting the formation of a complex between said RNA and said peptide or compound.

The invention relates, in addition, to a complex comprising a peptide of the invention, and a molecular structure specifically bound to said peptide, and which may, for example, be selected from peptide fragments, nucleotide fragments and chemical molecules such as those of the functionalized aromatic type. The complexing of a peptide of the invention which exhibits a high affinity with the viral RNA in particular, can prevent the attachment of this RNA and the expression of the latter. This complex therefore has application in the treatment of an HCV infection.

The invention and its characteristics are detailed in the examples which follow, and FIGS. 1 to 7.

Figure 6:
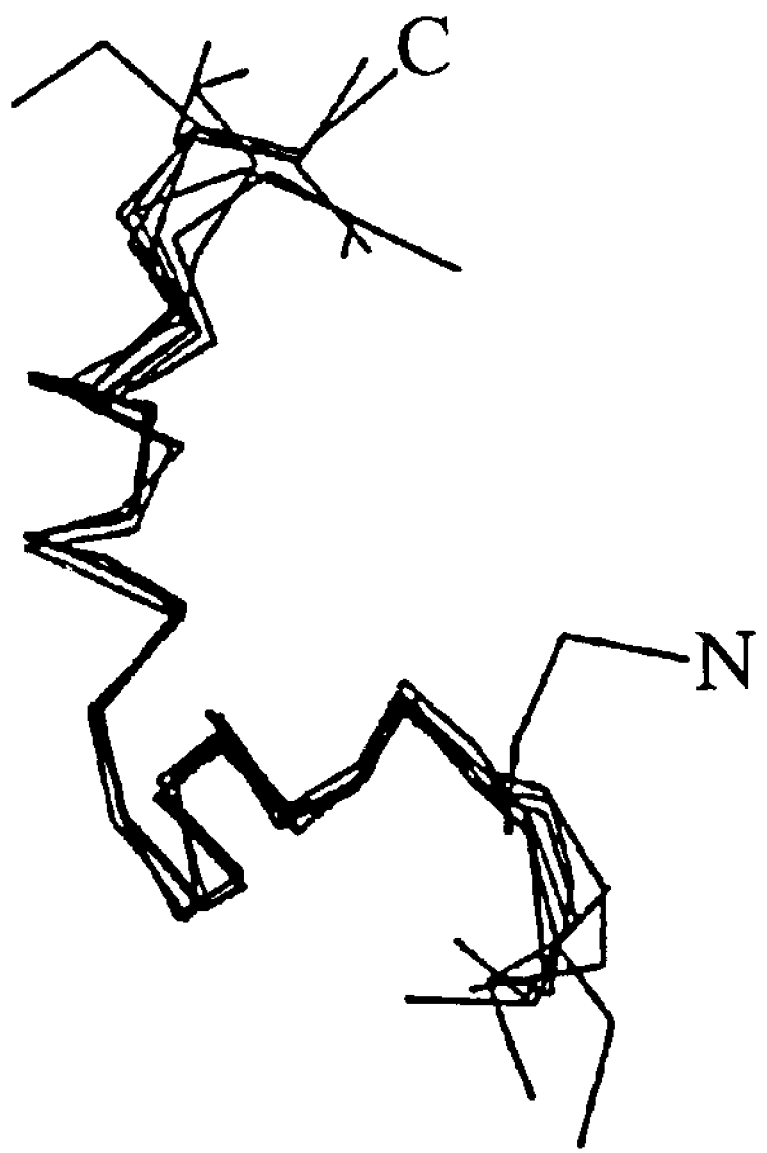
Figure 7:
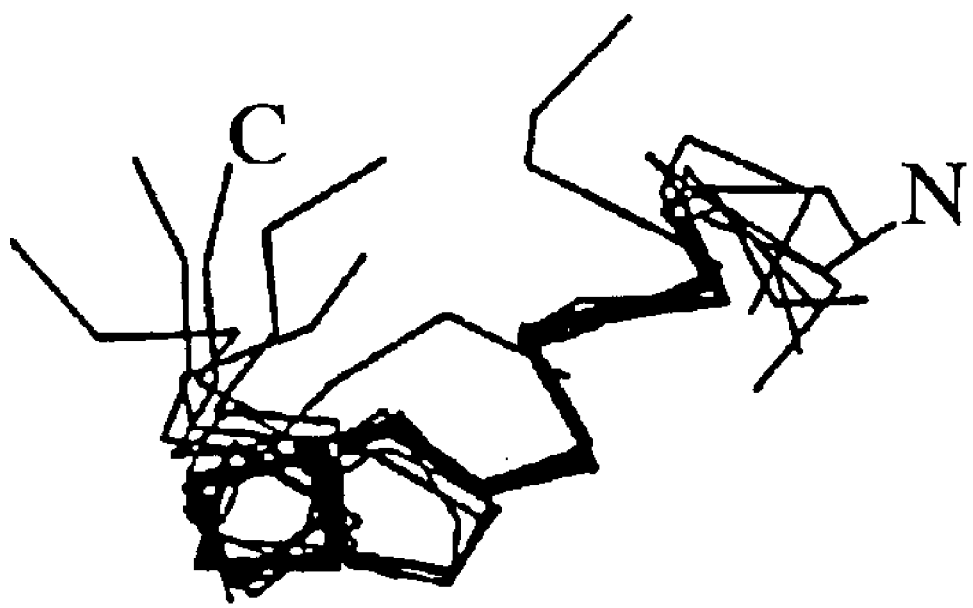

FIGS. 6 and 7 correspond to the superposition of 8 structures between Arg 18 and Leu 37, represented under two different angles; the RMSD of the principal chain between these residues is 0.64 Å.

FIGS. 4 to 7 are discussed in Example 4.

EXAMPLE 1

Structural Analysis of the Peptide SEQ ID NO: 2, by NMR and Molecular Modeling a) Search for sequence identity Attempts have been made to find out whether the studied peptide did not possess sequence homologies with proteins whose structure had already been determined and stored in the PDB databank (Protein Data Bank). It is generally thought that when two polypeptide sequences have more than 30% homology with each other, they possess very similar 3D structures. However, these analyses carried out using the search software FASTA 2.03 [D. J. Lipman and W. R. Pearson, Sciences, 227, 1435–1440 (1985)], show that there is no sequence of known 3D structure which is sufficiently homologous to the studied peptide to envisage a molecular modeling by homology.

b) Conditions for solvation of the peptide

The peptide was analyzed by placing it in a solution in 40% of 2,2,2-trifluoroethanol (TFE)/60% of H$_2$O, 0.1 M NaCl, 10 mM sodium phosphate, at pH 5.9 and at 20° C. These conditions make it possible to stabilize the secondary structures of the peptide while preserving the tertiary structure thereof.

c) Conditions for acquisition of the NMR spectra

All the NMR experiments were carried out on a VARIAN Unity+, 500 MHz, spectrometer equipped with ultrashims and with the aid of a 5 mm proton-carbon-nitrogen triple tuning probe equipped with Z gradient. The data are recorded with the aid of the VNMR software (version 5.1, marketed by VARIAN) on a SUN IPX work-station. The pulse sequences used are COSY, TOCSY, NOESY and ROESY. The NMR experiments were recorded in phased mode according to the States-TPPI method [D. Marion et al., J. Magn. Res., 85, 393–399 (1989)].

The experiments were carried out with a spectral width of 5500 Hz in both dimensions, 2048 data points in the dimension t2 and 512 increments in t1, each increment being accumulated 32 or 64 times. For the DQF-COSY experiments, 4K data points and 512 increments were recorded. A low-power presaturation at the frequency of water, applied during the relaxation time of a duration of 1.5 s (and during the mixing time in the NOESY experiments), was generally used to eliminate the resonance of the solvent. For the TOCSY experiments, the isotropic mixture is an MLEV-17 sequence for which a delay Δ equal to 2.6 times the pulse duration at 90° is inserted between the pulses [clean-TOCSY; C. Griesinger et al., J. Am. Chem. Soc., 110, 7870–7872 (1988)]. A trim-pulse of 2 ms precedes the mixing period whose duration is generally set at 80 ms. For the ROESY experiments, the spin-lock is achieved by a continuous irradiation having a power of between 3 and 4 kHz. Two pulses at 90° are placed on either side of the mixing period (compensated ROESY).

d) Molecular modeling

All the molecular modeling steps were carried out according to standard procedures for the X-plor program version 3.1 [A. T. Brünger, in X-plor, A System for Crystallography and NMR, Yale University Press, New Haven (1992)] on IBM rs6000 model 560 or SUN Sparc 20 stations.

The generation of the topology consists in using a series of theoretical information (description of the atoms, attribution of the covalent bonds, of the valency angles) to model a peptide having an ideal geometry. The following step uses the method of geometry of distances. The distance intervals between protons determined by NMR and the theoretical distance intervals linked to the primary structure (length of the bonds, distances due to the rigidity of the aromatic rings, and the like) are assembled. There is a random sorting of a set of distances between the authorized distance intervals. These distances are then converted to Cartesian coordinates for each atom in the molecule. An optimization step is applied; it consists in minimizing a target function which represents the errors on the experimental distances observed in the generated structures. As a result of the random sorting of the distance set, no single structure, but a family of structures is generated so as to explore any conformational space as widely as possible. These structures roughly satisfy the experimental distance constraints; however, there are still often imperfections in their covalent geometry and their potential energy is generally high. A regulation of the structures by molecular dynamics with simulated annealing is then applied. It consists of a gradual increase in the temperature up to 2000° K for 9 picoseconds, in steps of 50° K, and then of an equilibration for 12 picoseconds and a cooling to 250° K in steps of 25° K for 10 picoseconds. A second step of refining the structures by simulated annealing is carried out at 1000° K for 50 picoseconds, followed by a minimization of the energy by 500 Powell cycles. In this step, the weight of the Van der Waals interactions is kept low. Up until now, a simplified parameter was used to rapidly generate structures compatible with the NMR data (for example, during the simulated annealing step, all the electrostatic energy terms were suppressed). The last step in this modeling therefore consists in minimizing the potential energy of the different structures obtained.

EXAMPLE 2

Antigenicity of the Peptide SEQ ID NO: 2

The antigenic properties of the peptide were analyzed by the Applicant by the ELISA tests described below and carried out with sera obtained from people infected with HCV. For each of the ten sera tested, an additional well, in which the peptide has not been deposited, serves as internal control.

a) Protocol for the ELISA tests

This technique makes it possible to demonstrate the presence of specific antibodies in the serum or the plasma from an individual and, by extension, the presence of the corresponding antigen in their body.

The wells of a microtiter plate of "NUNC maxisorb" trademark are saturated with 100 μl of a carbonate buffer solution, pH 9.6, containing the peptide (10 µg/ml) for 2 hours. The plate is then emptied and then washed with the aid of a wash buffer containing 0.05% Tween 20. The wells are saturated with 100 µl of wash buffer supplemented with 10% goat serum (v/v), incubated for 30 minutes at 37° C., and then washed again as above. The sera to be analyzed are diluted in an appropriate manner with the saturation buffer and then incubated in the wells for 1 hour at 37° C. The wells are again washed. The solution of conjugate (goat IgG anti-human IgG labeled with peroxydase) at a dilution of 1/1000 in the saturation buffer is then added. After 10 minutes, the reaction is blocked with 50 µl of $H_2SO_4$ and the optical density is read at 492 nm.

b) Results

Table 1 below groups together the results of the ELISA tests, expressed as optical density (OD) read at 492 nm after reaction of peroxydase. This table shows that the peptide reacts strongly with practically all the sera containing anti-nucleocapsid antibodies since the optical densities (OD) observed for this peptide are generally much higher than those for the control well. The serum H662 with which the peptide does not react is of type 1+, that is to say a serum listed as being only slightly reactive toward the nucleocapsid.

It can be finally noted that the peptide does not exhibit cross-reactivity with the two sera called "neg" which do not contain antibodies directed against the nucleocapsid.

TABLE 1

| Serum | Dilution | Peptide | Control |
|---|---|---|---|
| *4+H8 | | 0.097 | 0.025 |
| 4+H69 | 1/1000 | 0.455 | 0.018 |
| 4+H666 | | 0.330 | 0.016 |
| *3+H1 | 1/100 | 0.375 | 0.036 |
| 3+H3 | | 0.726 | 0.070 |
| *2+H654 | | 0.251 | 0.026 |
| *1+H661 | 1/100 | 0.050 | 0.043 |
| 1+H662 | | 0.028 | 0.031 |
| neg H4 | 1/100 | 0.042 | 0.051 |
| neg H647 | | 0.026 | 0.028 |

*The sera are classified according to their reactivity and are given an index: the sera with index 4+ react strongly, the sera with index 1+ react weakly toward a reference confirmation test, for example RIBA 3 (marketed by ORTHO DIAGNOSTIC).

EXAMPLE 3

NMR Characterization of the Three-Dimensional Structure of a Peptide of the Invention For experimental reasons, a peptide called Capsid (15–41), longer than the reference peptide (SEQ ID NO: 2) previously identified, by two amino acids, was synthesized and then characterized by NMR, according to the procedure and the materials identified in Example 1, by placing said peptide in 40% of TFE/60% $H_2O$, 0.1 M NaCl, 10 mM sodium phosphate, at pH 5.9 and at 20° C.

Figure 1:
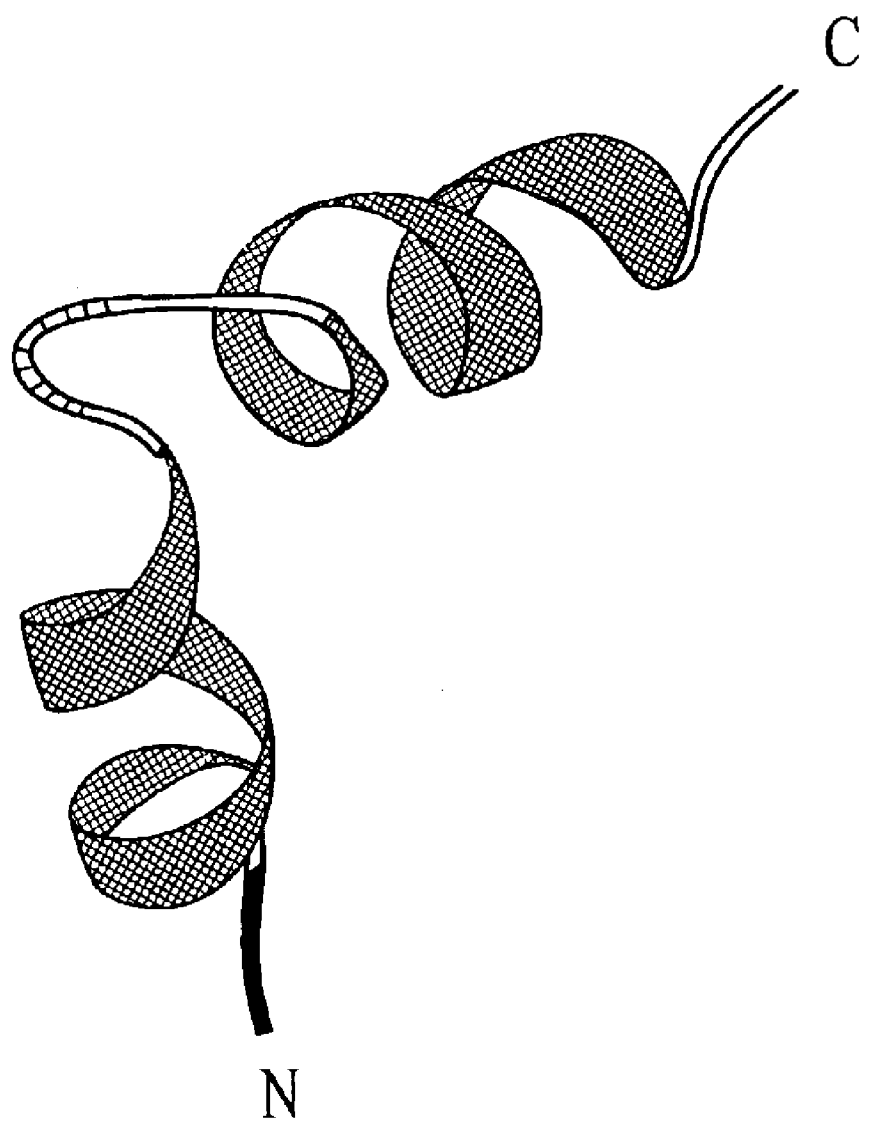
FIG. 1 is a schematic representation with the aid of the Molscript software of the three-dimensional structure of the peptide of SEQ ID NO: 2, in solution in the 40% mixture (v/v) of 2,2,2-trifluoroethanol (TFE)/60% buffer:100 mM NaCl, 10 mM sodium phosphate, at pH 5.9.
Figure 2:
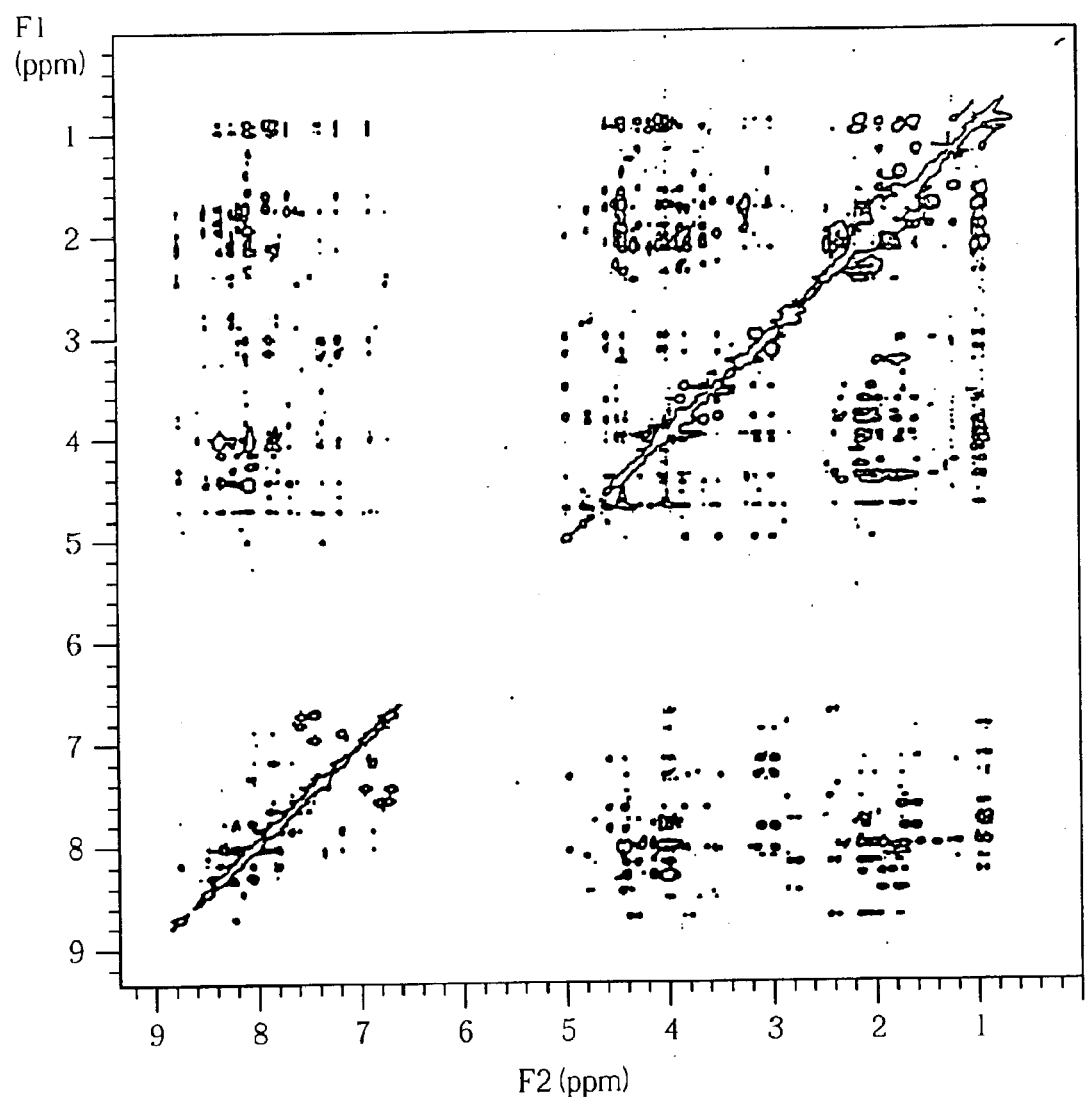
FIGS. 2 and 3 represent the NMR spectra of the peptide Capsid (15–41) which are discussed in Example 3.

FIG. 2 shows that the NOESY spectrum of the peptide, recorded with a mixing time of 250 ms, over 2048 points in the dimension t1 and 512 in the dimension t2. In t1 and t2, a zero filling respectively at 4 K and 2 K was applied.

The filtering is of the square sine type in both dimensions. This spectrum is more particularly representative of the secondary structure of the peptide considered.

Figure 3:
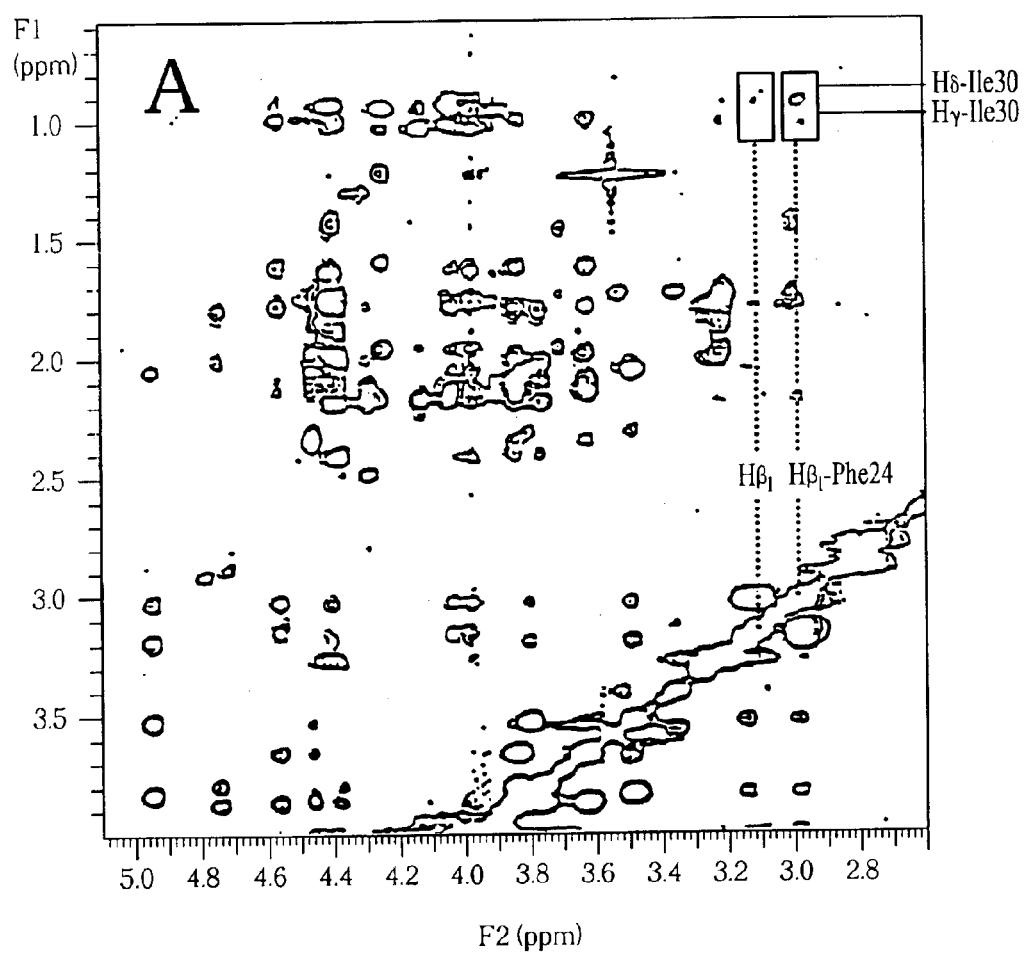
Figure 4:
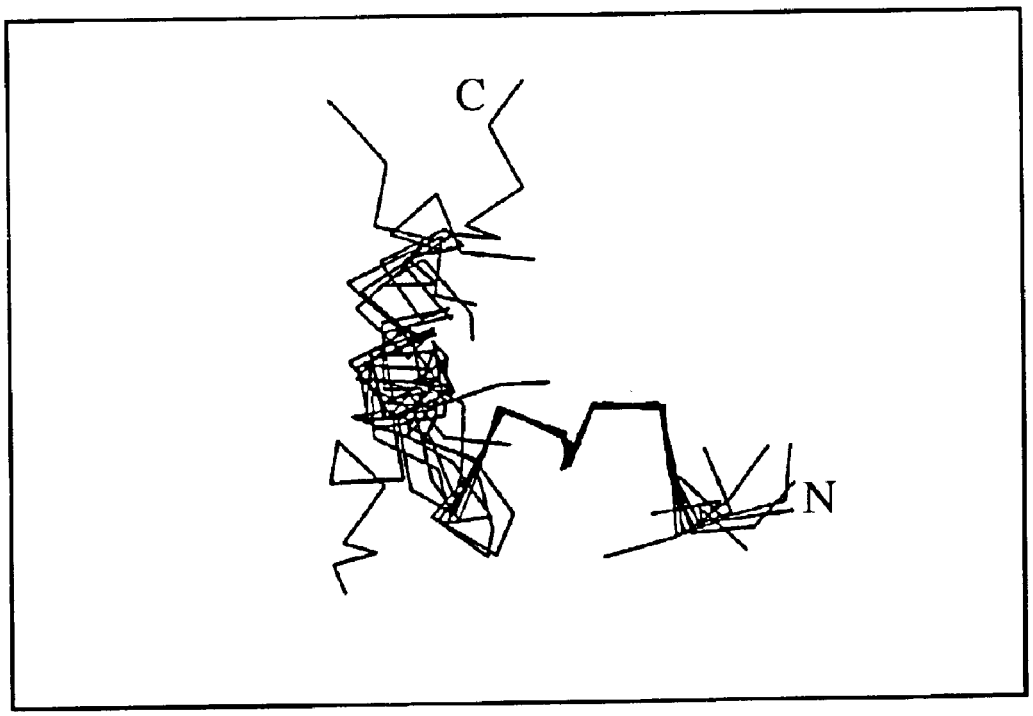
FIG. 4 represents the superposition of 8 structures between Arg 18 and Phe 24; the RMSD of the principal chain between these residues is 0.29 Å.
Figure 5:
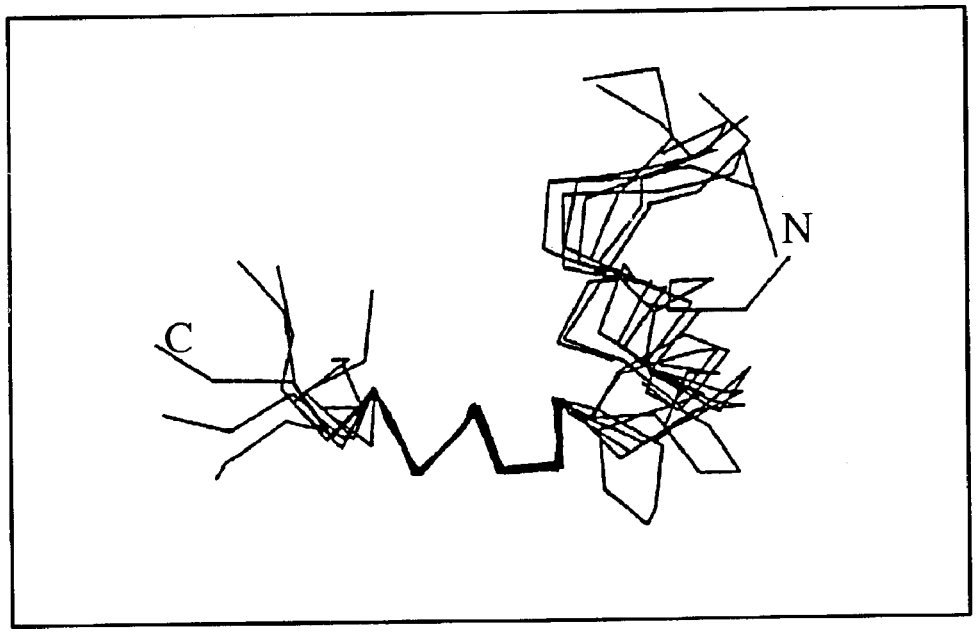
FIG. 5 represents the superposition of the same 8 structures as in FIG. 4, between Glu 29 and Leu 37; the RMSD of the principal chain between these residues is 0.39 Å.

The spectrum according to FIG. 3 was recorded with a mixing time of 250 ms. The correlations between the β protons of Phe 24, and the γ and δ protons of Ile 30 were indicated, and are characteristic of the tertiary structure previously defined.

EXAMPLE 4

Molecular Modeling of the Three-Dimensional Structure of the Peptide Capsid (15–41)

The molecular modeling of the peptide Capsid (15–41) was carried out using 252 and 268 stresses respectively (Table 2 below). Out of the 50 structures generated for each peptide, 32 accepted structures are obtained for the peptide Capsid (15–41).

The peptide Capsid (15–41) model shows that this peptide indeed contains the two helices of the peptide and that these two helices are indeed kept perpendicular to each other. The 3D helix-loop-helix unit is therefore found for this peptide.

Table 2 gives the NMR stresses for the peptide Capsid (15–41) in which the intra-residual stresses (i, i) correspond to the protons carried by the same amino acid residue; the sequential stresses (i, i+1) link the protons situated on two adjacent residues; the so-called medium-range stresses (i, i+2 to i+4) involve protons separated by at most four residues in the sequence; and the long-range type of stresses (i, i>i+4) link the protons of residues separated by more than 4 amino acids.

TABLE 2

| Type of stress | |
|---|---|
| Intra-residual (i, i) | 70 |
| Sequential (i, i + 1) | 97 |
| Medium (i, i + 2 to i + 4) | 73 |
| Long (i, i > i + 4) | 12 |
| Total | 252 |

What is claimed is:

1. A method of detecting and/or quantifying, in a sample, all or part of the RNA of the hepatitis C virus, comprising: bringing said sample into contact with a peptide recognized by antibodies directed against a polypeptide comprising the sequence of amino acids 2–45 of the N-terminal end of the Core or nucleocapsid protein (p21) of the hepatitis C virus (HCV) (SEQ ID NO: 1), wherein said peptide comprises a peptide sequence equivalent but not identical to SEQ ID NO: 2, or said peptide consists of the peptide sequence SEQ ID NO: 2, said peptide sequence comprising a tertiary structure consisting of at least a first peptide fragment having a secondary structure in the form of an α helix, a second peptide fragment having a secondary structure in the form of an α helix and a third joining peptide fragment linking the two α helices, these two α helices being substantially perpendicular to each other in space, excluding (i) all protein or peptide compounds comprising or consisting of the N-terminal end of the p21 protein, this end being considered as starting at the amino acid at position 1 or the amino acid at position 2, and (ii) the sequence SEQ ID NO: 11, and detecting the formation of a complex between said RNA and said peptide.

2. A method according to claim 1, wherein the two α helices form an angle of 90°±10°.

3. A method according to claim 1, wherein the third fragment is chosen from loops and elbows.

4. A method according to claim 1, wherein the peptide sequence equivalent to SEQ ID NO: 2 is selected from the group consisting of sequences SEQ ID NO: 3 to SEQ ID NO: 10.

5. A method according to claim 1, wherein said peptide consists of a peptide sequence equivalent to SEQ ID NO: 2.

6. A method according to claim 1, wherein said peptide consists of the peptide sequence SEQ ID NO: 2.

7. A monoclonal or polyclonal antibody capable of being obtained by in vivo immunization of an animal or by in vitro immunization with an immunogenic compound comprising a peptide of SEQ ID NO: 2, said peptide having a tertiary structure having at least a first peptide fragment having a secondary structure in the form of an α helix, a second peptide fragment having a secondary structure in the form of an α helix and a third peptide fragment linking the two α helices, these two α helices being substantially perpendicular to each other in space, wherein said antibody is directed against SEQ ID NO: 2.

8. A pharmaceutical composition comprising an antibody according to claim 7.

9. A method of detecting and/or quantifying, in a sample, antigens of HCV, comprising bringing said sample into contact with antibodies according to claim 7, and detecting the formation of an immune complex between said antigens and said antibodies.

10. A method according to claim 1, wherein said peptide is an immunogenic compound capable of inducing the production of antibodies directed against a polypeptide comprising the sequence of amino acids 2–45 of the N-terminal end of the Core protein (p21) of the hepatitis C virus (HCV) (SEQ ID NO: 1).

11. A complex comprising:

a peptide recognized by antibodies directed against a polypeptide comprising the sequence of amino acids 2–45 of the N-terminal end of the Core or nucleocapsid protein (p21) of the hepatitis C virus (HCV) (SEQ ID NO: 1), wherein said peptide comprises a peptide sequence equivalent but not identical to SEQ ID NO: 2, or said peptide consists of the peptide sequence SEQ ID NO: 2, said peptide sequence comprising a tertiary structure consisting of at least a first peptide fragment having a secondary structure in the form of an α helix, a second peptide fragment having a secondary structure in the form of an α helix and a third joining peptide fragment linking the two α helices, these two α helices being substantially perpendicular to each other in space, excluding (i) all protein or peptide compounds comprising or consisting of the N-terminal end of the p21 protein, this end being considered as starting at the amino acid at position 1 or the amino acid at position 2, and (ii) the sequence SEQ ID NO: 11, and a molecular structure specifically bound to said peptide, said molecular structure being selected from the group consisting of peptide fragments, nucleotide fragments and chemical molecules.

12. A complex according to claim 11, said molecular structure being a nucleotide fragment or a chemical molecule.

13. A complex according to claim 11, wherein said chemical molecule is a functionalized aromatic compound.

14. A method for treating an infection with HCV, comprising administering to a patient a composition containing a peptide recognized by antibodies directed against a polypeptide comprising the sequence of amino acids 2–45 of N-terminal end of the Core or nucleocapsid protein (p21) of the hepatitis C virus (HCV) (SEQ ID NO: 1), wherein said peptide comprises a peptide sequence equivalent but not identical to SEQ ID NO: 2, or said peptide consists of the peptide sequence SEQ ID NO: 2, said peptide sequence comprising a tertiary structure consisting of at least a first peptide fragment having a secondary structure in the form of an α helix, a second peptide fragment having a secondary structure in the form of an α helix and a third joining peptide fragment linking the two α helices, these two α helices being substantially perpendicular to each other in space, excluding (i) all protein or peptide compounds comprising or consisting of the N-terminal end of p21 protein, this end being considered as starting at the amino acid at position 1 or the amino acid at position 2, and (ii) the sequence SEQ ID NO: 11.

15. A method according to claim 14, wherein said peptide is an immunogenic compound capable of inducing the production of antibodies directed against a polypeptide comprising the sequence of amino acids 2–45 of the N-terminal end of the Core protein (p21) of the hepatitis C virus (HCV) (SEQ ID NO: 1).

16. A method for treating an infection with HCV, comprising administering a composition containing an antibody according to claim 7 to a patient.

17. A complex according to claim 11, wherein the two α helices form an angle of 90°±10°.

18. A complex according to claim 11, wherein the third fragment is chosen from loops and elbows.

19. A complex according to claim 11, wherein the peptide sequence equivalent to SEQ ID NO: 2 is selected from the group consisting of sequences SEQ ID NO: 3 to SEQ ID NO: 10.

20. A complex according to claim 11, wherein said peptide consists of a peptide sequence equivalent to SEQ ID NO: 2.

21. A complex according to claim 11, wherein said peptide consists of the peptide sequence SEQ ID NO: 2.

22. A method according to claim 14, wherein the two α helices form an angle of 90°±10°.

23. A method according to claim 14, wherein the third fragment is chosen from loops and elbows.

24. A method according to claim 14, wherein the peptide sequence equivalent to SEQ ID NO: 2 is selected from the group consisting of SEQ ID NO: 3 to SEQ ID NO: 10.

25. A method according to claim 14, wherein said peptide consists of a peptide sequence equivalent to SEQ ID NO: 2.

26. A method according to claim 14, wherein said peptide consists of a peptide sequence SEQ ID NO: 2.

* * * * *

SEQUENCE LISTING

<160> NUMBER OF SEQ ID NOS: 11

<210> SEQ ID NO 1
<211> LENGTH: 44
<212> TYPE: PRT
<213> ORGANISM: Hepatitis C virus
<300> PUBLICATION INFORMATION:
<301> AUTHORS: Ogata, N. et al.

<302> TITLE: Nucleotide Sequence and Mutation Rate of the H Strain
      of Hepatitis Virus
<303> JOURNAL: Proc. Natl. Acad. Sci. U.S.A.
<304

<213> ORGANISM: Hepatitis C virus

<400> SEQUENCE: 6

Thr Asn Arg Arg Pro Gln Asp Val Lys Phe Pro Gly Gly Gly Gln Ile
 1               5                  10                  15

Val Gly Gly Val Tyr Val Leu Pro Arg
            20                  25

<210> SEQ ID NO 7
<211> LENGTH: 25
<212> TYPE: PRT
<213> ORGANISM: Hepatitis C virus

<400> SEQUENCE: 7

Thr Tyr Arg Arg Pro Gln Asp Val Lys Phe Pro Gly Gly Gly Gln Ile
 1               5                  10                  15

Val Gly Gly Val Tyr Val Leu Pro Arg
            20                  25

<210> SEQ ID NO 8
<211> LENGTH: 25
<212> TYPE: PRT
<213> ORGANISM: Hepatitis C virus

<400> SEQUENCE: 8

Thr Ile Arg Arg Pro Gln Asp Val Lys Phe Pro Gly Gly Gly Gln Ile
 1               5                  10                  15

Val Gly Gly Val Tyr Val Leu Pro Arg
            20                  25

<210> SEQ ID NO 9
<211> LENGTH: 25
<212> TYPE: PRT
<213> ORGANISM: Hepatitis C virus

<400> SEQUENCE: 9

Thr Ile Arg Arg Pro Gln Asp Ile Lys Phe Pro Gly Gly Gly Gln Ile
 1               5                  10                  15

Val Gly Gly Val Tyr Ile Leu Pro Arg
            20                  25

<210> SEQ ID NO 10
<211> LENGTH: 25
<212> TYPE: PRT
<213> ORGANISM: Hepatitis C virus
<220> FEATURE:
<221> NAME/KEY: SITE
<222> LOCATION: (8)
<223> OTHER INFORMATION: Xaa is Ile or Val or Leu
<220> FEATURE:
<221> NAME/KEY: SITE
<222> LOCATION: (16)
<223> OTHER INFORMATION: Xaa is Ile or Val or Leu
<220> FEATURE:
<221> NAME/KEY: SITE
<222> LOCATION: (17)
<223> OTHER INFORMATION: Xaa is Ile or Val or Leu
<220> FEATURE:
<221> NAME/KEY: SITE
<222> LOCATION: (20)
<223> OTHER INFORMATION: Xaa is Ile or Val or Leu
<220> FEATURE:
<221> NAME/KEY: SITE
<222> LOCATION: (22)
<223> OTHER INFORMATION: Xaa is Ile or Val or Leu
<220> FEATURE:
<221> NAME/KEY: SITE -continued

```
<222> LOCATION: (23)
<223> OTHER INFORMATION: Xaa is Ile or Val or Leu

<400> SEQUENCE: 10

Thr Asn Arg Arg Pro Gln Asp Xaa Lys Phe Pro Gly Gly Gly Gln Xaa
 1               5                  10                  15

Xaa Gly Gly Xaa Tyr Xaa Xaa Pro Arg
            20              25

<210> SEQ ID NO 11
<211> LENGTH: 32
<212> TYPE: PRT
<213> ORGANISM: Hepatitis C virus

<400> SEQUENCE: 11

Gln Arg Lys Thr Lys Arg Asn Thr Asn Arg Arg Pro Gln Asp Val Lys
 1               5                  10                  15

Phe Pro Gly Gly Gly Gln Val Val Gly Gly Val Tyr Leu Leu Pro Arg
                20                  25                  30
```